United States Patent [19]
Campbell et al.

[11] Patent Number: 5,496,349
[45] Date of Patent: Mar. 5, 1996

[54] METHOD AND SYSTEM FOR AUTOMATIC OR SEMI-AUTOMATIC DEFILBRILLATION USING REDUNDANT PROCESSING

[75] Inventors: Dean D. Campbell, Seattle; Robert A. Wiley, Tukwila, both of Wash.

[73] Assignee: Physio-Control Corporation, Redmond, Wash.

[21] Appl. No.: 209,774

[22] Filed: Mar. 11, 1994

[51] Int. Cl.$^6$ .................................................... A61N 1/39
[52] U.S. Cl. .................................................................. 607/5
[58] Field of Search ............................... 607/5, 7, 8, 63; 128/908, 705

[56] References Cited

U.S. PATENT DOCUMENTS

| | | | |
|---|---|---|---|
| Re. 30,372 | 8/1980 | Denniston et al. | 607/6 |
| Re. 30,387 | 8/1980 | Mirowski et al. | 607/6 |
| 5,097,830 | 3/1992 | Eikefjord et al. | 607/8 |

*Primary Examiner*—William E. Kamm
*Assistant Examiner*—Jeffrey R. Jastrzab

[57] ABSTRACT

A method and system for automatic or semi-automatic defibrillation using redundant processing is provided. In a preferred embodiment, two microprocessors each separately analyze electrocardiogram signals from a patient in order to separately determine whether the patient should be treated. If both microprocessors determine that the patient should be treated, a treatment subsystem defibrillates the patient by delivering a defibrillation charge to the patient. In a semi-automatic embodiment, the treatment subsystem only delivers a defibrillation charge to the patient if a human operator has responded to a visual indication that the patient should be treated by manually activating the defibrillator.

37 Claims, 3 Drawing Sheets

5,496,349

METHOD AND SYSTEM FOR AUTOMATIC OR SEMI-AUTOMATIC DEFILBRILLATION USING REDUNDANT PROCESSING

TECHNICAL FIELD

The invention relates generally to a method and system for automatically analyzing electrocardiogram (ECG) signals to determine whether to treat a patient with a defibrillator, and, more specifically, to a method and system for automatically analyzing ECG signals to determine whether to treat a patient with a defibrillator using redundant processing.

BACKGROUND OF THE INVENTION

Devices are presently available for automatically analyzing electrocardiogram (ECG) signals to determine whether to treat a patient with a defibrillator. See, for example, U.S. Pat. No. 4,919,144, entitled "Defibrillator ECG Interpreter," which is hereby incorporated by reference. Such a devices use monitoring electrodes connected to a patient to collect ECG signals from the patient. The device then analyzes the collected ECG signals. If the device, by its analysis, determines that the patient should be treated, the device either defibrillates the patient or it advises an operator to trigger the device to defibrillate the patient. Defibrillation is accomplished by delivering an electrical charge to the patients through defibrillation electrodes connected to the patient. (In some cases, a single set of electrodes serves as both the monitoring electrodes and the defibrillation electrodes.)

Such devices use a single microprocessor executing an ECG analysis program to determine whether to treat the patient. While such devices commonly execute the analysis program multiple times in order to avoid treating the patient in response to spurious, false-positive ECG signals, failure of the single processor can cause these devices to erroneously determine that the patient should be treated and proceed to treat the patient erroneously. Failure of the single processor can also cause the devices to erroneously omit treatment of the patient.

SUMMARY OF THE INVENTION

It is an object of the invention to provide a method and system for determining, using redundant processing, whether a patient should be defibrillated.

It is another object of the invention to provide a method and system for defibrillating a patient if at least two processors separately determine that the patient should be defibrillated.

It is yet another object of the invention to provide a method and system in a defibrillator for determining whether a patient is correctly connected to the defibrillator by the appropriate dual-purpose electrodes.

It is a further object of the invention to provide a method and system in a computer system for automatic or semi-automatic defibrillation in which the two microprocessors that determine whether the patient should be defibrillated perform reciprocal diagnostics.

It is yet a further object of the invention to provide a method and system for automatic or semiautomatic defibrillation in which a charging circuit accumulates a charge of the desired energy under the simultaneous control of two microprocessors.

These and other objects which will become apparent as the invention is more fully described below, are provided by a method and system for automatic or semi-automatic defibrillation using redundant processing. In a preferred embodiment, two microprocessors each separately analyze electrocardiogram signals from a patient in order to separately determine whether the patient should be treated. If both microprocessors determine that the patient should be treated, a treatment subsystem defibrillates the patient by delivering a defibrillation charge to the patient. In a semi-automatic embodiment, the treatment subsystem only delivers a defibrillation charge to the patient if a human operator has responded to a visual indication that the patient should be treated by manually activating the defibrillator.

DETAILED DESCRIPTION OF THE INVENTION

A method and system for semi-automatic defibrillation using redundant processing is provided. In a preferred embodiment, a multiple processor device (MPD) contains at least two separate microprocessors (processors) for redundantly analyzing electrocardiogram (ECG) signals and controlling defibrillation. The processors perform separate analyses of the same ECG signals, and communicate regularly across an inter-processor communications link (link) to assure the consistency of the ongoing results of each processor's analysis. If the processors agree throughout their analyses and both reach a final treat result, the MPD concludes that the patient should be treated by delivering an electrical charge to the patient. If the analyses of the processors diverge at any point, the MPD aborts treatment, dissipating any accumulated charge by discharging it internally. Became processor analysis divergence implicates the failure of one of the processors, the MPD further disables itself pending service.

Figure 1:
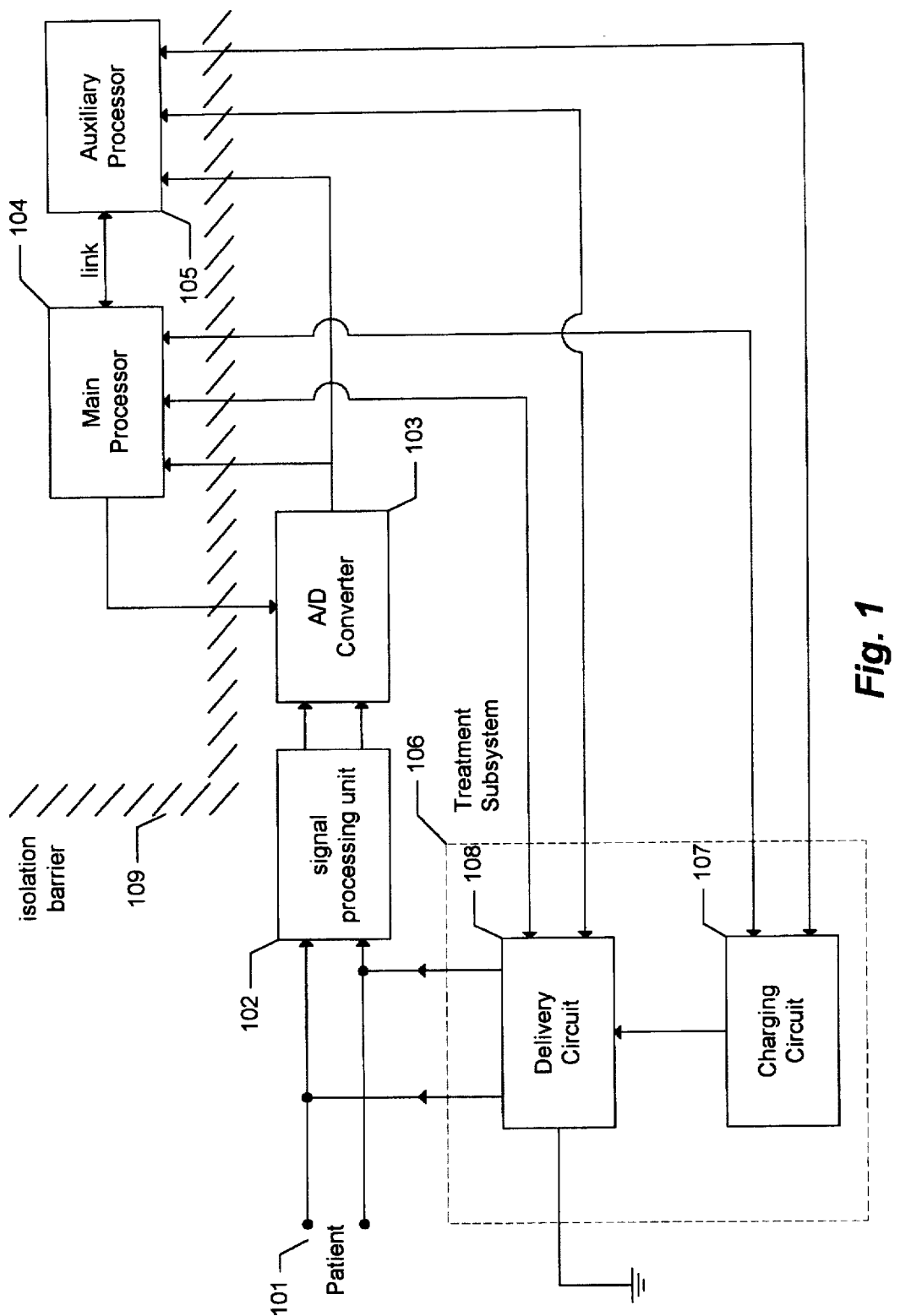
FIG. 1 is a block diagram showing an overview of the components of the multiple processor device.

FIG. 1 is a block diagram showing an overview of the components of the MPD. The patient 101 generates ECG signals, which are conducted by two dual-purpose electrodes to a signal processing unit 102. The signal processing unit 102 amplifies and filters the analog signal from the electrodes. The amplified and filtered analog signal is conducted to an analog to digital converter (A/D converter) 103. When the A/D converter 103 receives a conversion strobe from a main processor 104, the A/D converter 103 converts the analog voltage from the signal processing unit 102 into a digital representation that it makes available on its data bus to both the main processor 104 and an auxiliary processor 105. The conversion strobe preferably occurs every 10 milliseconds. The A/D converter 103 may output its data in either parallel or serial format. If the data is output in serial format, a shift register (not shown) is interposed between the A/D converter 103 and the processors 104, 105 to convert serial data from the A/D converter 103 to parallel data for input to each processor. The processors 104, 105, as well as other high voltage components such as the power supply, are separated from the rest of MPD by an isolation barrier 109, designed to protect the patient from unintended dangerous voltages. Both processors 104, 105 read the digital representation from the output generated the A/D converter 103, called a sample, and incorporate it in their analyses. Throughout their analyses, the processors 104, 105 communicate via a communication link (link) to assure that they are operating correctly. The link is preferably an RS-232 line. Both processors 104, 105 periodically transmit a signal to the other processor indicating that the processor is operating properly. If either processor 104, 105 fails to receive such a signal from the other processor for a period of time exceeding a signaling threshold, the processor that did not receive a signal enters a DISABLED STATE (described below), in which the MPD cannot continue normal operation. If the analysis of the main processor 104 reaches a tentative treat result, both processors 104, 105 together trigger a charging circuit 107 in the treatment subsystem 106, causing it to begin accumulating a charge. If the processors agree throughout their analyses and both reach a final treat result, the MPD either defibrillates the patient (in the case of an automatic defibrillator) or advises an operator to manually initiate defibrillation (in the case of a semi-automatic defibrillator). In either case, both processors 104, 105, trigger a delivery circuit 108 of the treatment subsystem, causing the delivery circuit 108 to deliver the charge accumulated in the treatment subsystem 106 to the patient via the dual-purpose electrodes. Both processors 104, 105 must signal the delivery circuit for it to deliver the charge accumulated in the treatment subsystem 106 to the patient. If the analyses of the processors 104, 105 diverge at any point, either the main processor 104 or the auxiliary processor 105 triggers an internal discharge function of the treatment subsystem 106, causing it to dissipate the accumulated charge by discharging it internally. Because processor analysis divergence implicates the failure of one of the processors 104, 105, the MPD further disables itself pending service. The MPD further includes an analyze button switch (not shown) and, in the case of a semi-automatic defibrillator, a deliver button switch (not shown), which each generate a signal that is made available to both processors 104, 105 to cause the processors to trigger the delivery circuit 108.

Figure 2:
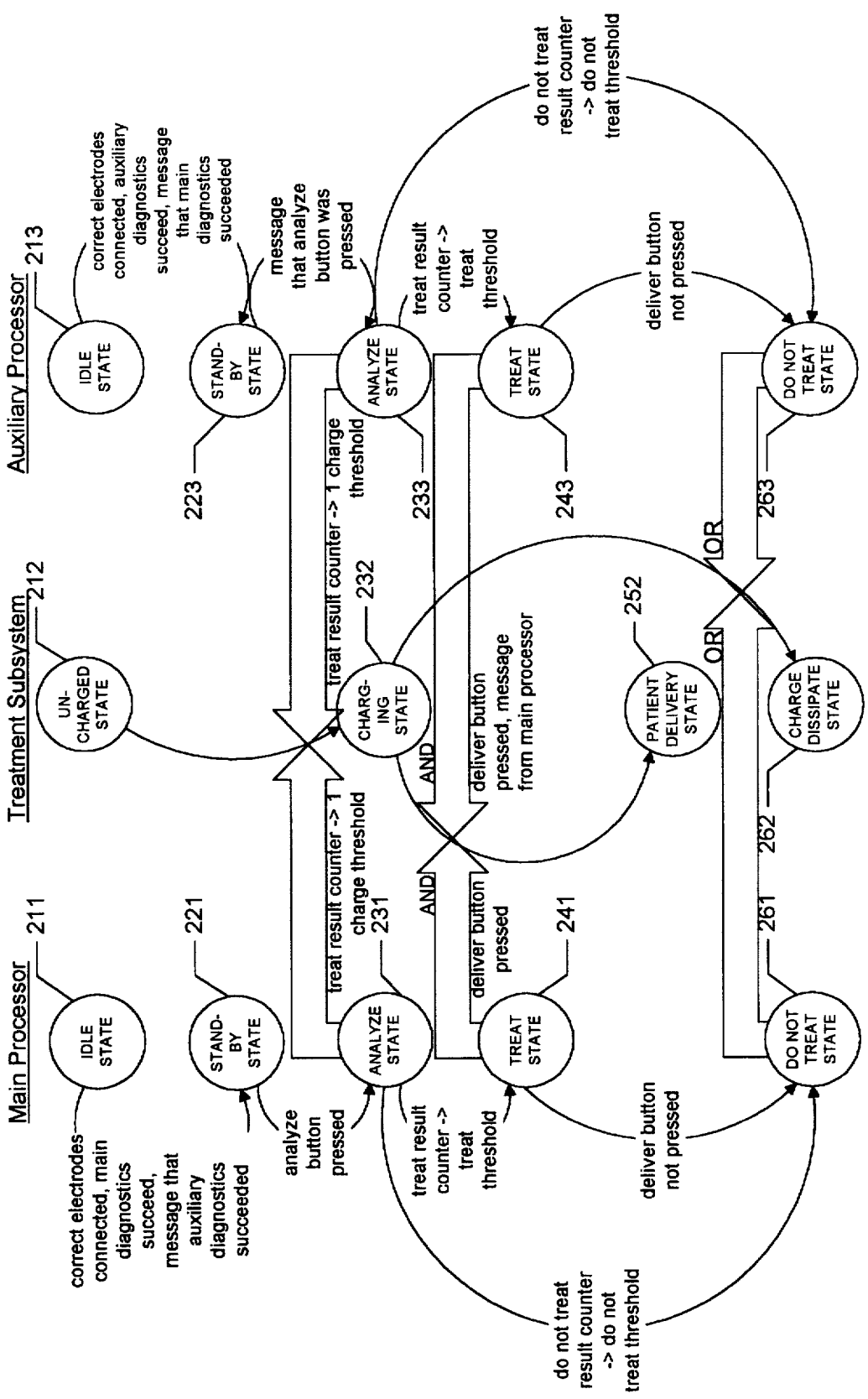
FIG. 2 is an overview state diagram showing the possible states of the MPD.

FIG. 2 is an overview state diagram showing the possible states of the MPD. The possible states of the MPD are all permutations of the possible states of three constituent parts of the MPD: the main processor, the treatment subsystem and the auxiliary processor. States 211, 221, 231, 241, and 261 represent states of the main processor. States 212, 232, 252, and 262 represent states of the treatment subsystem. States 213, 223, 233, 243, and 263 represent states of the auxiliary processor.

The diagram shows that the main processor 104 begins in IDLE STATE 211, the treatment subsystem 106 begins in UNCHARGED STATE 212, and the auxiliary processor 105 begins in IDLE STATE 213. The IDLE STATE 211, 213 is designed to determine whether conditions are correct for an operator to initiate ECG analysis. In the IDLE STATE 211, the main processor 104 proceeds to STANDBY STATE 221 if it determines that (a) the MPD is connected to a patient by the correct, dual-purpose electrodes, as determined by the impedance across the inputs of the A/D converter 103 (FIG. 1); (b) its own diagnostic routines (diagnostics) have succeeded; and (c) it has received from the auxiliary processor 105 a message indicating that the auxiliary processor's diagnostics have succeeded. If the impedance across the A/D converter 103 inputs does not indicate that the MPD is connected to a patient by the correct, dual-purpose electrodes or the main processor 104 has not received a message from the auxiliary processor 105 about the results of the auxiliary processor's diagnostics, the main processor 104 remains in the IDLE STATE 211. If, however, the main processor's diagnostics fail or the main processor 104 receives a message that the auxiliary processor's diagnostics have failed, the main processor 104 enters a DISABLED STATE (not shown). The DISABLED STATE is designed to inhibit the immediate operation of the MPD and store information about the failure in a failure log for later use in diagnosing the failure. The main processor 104 cannot exit the DISABLED STATE until the operator activates a reset function of the MPD.

Similarly, in the IDLE STATE 213, the auxiliary processor 105 proceeds to STANDBY STATE 223 if it determines that (a) the MPD is connected to a patient by the correct, dual-purpose electrodes; (b) its own diagnostic routines (diagnostics) have succeeded; and (c) it has received from the main processor 104 a message indicating that the main processor's diagnostics have succeeded. If the impedance across the A/D converter 103 inputs does not indicate that the MPD is connected to a patient by the correct, dual-purpose electrodes or the auxiliary processor 105 has not received a message from the main processor about the results of the main processor's diagnostics, the auxiliary processor 105 remains in the IDLE STATE 213. If, however, the auxiliary processor's diagnostics fail or the auxiliary, processor 105 receives a message that the main processor's diagnostics have failed, the auxiliary processor 105 proceeds to a DISABLED STATE (not shown) in which information about the failure is stored in the failure log. Like the main processor 104, the auxiliary processor 105 cannot exit from its DISABLED STATE until the operator activates the reset function of the MPD. The processors 104, 105 also preferably exchange status messages periodically. If one processor fails to send a status message indicating that it is functioning properly, the other processor proceeds to the DISABLED STATE.

The STANDBY STATE 221, 223 is designed to wait for the operator to initiate ECG analysis by pressing an analyze button. In the STANDBY STATE 221, the main processor 104 waits for the operator to press the analyze button. When the operator presses the analyze button, the main processor 104 (a) proceeds to ANALYZE STATE 231 and (b) sends a message to the auxiliary processor 105 informing it that the analyze button has been pressed. In the STANDBY STATE 223, when the auxiliary processor 105 receives the message from the main processor 104 informing it that the analyze button has been pressed, the auxiliary processor 105 also proceeds to ANALYZE STATE 233.

The operation of the main processor 104 and the auxiliary processor 105 while in the ANALYZE STATE 231, 233 is described in detail below in conjunction with FIG. 3. Briefly, in the ANALYZE STATE 231, 233, each processor 104, 105 executes the same ECG analysis program repeatedly to analyze the ECG signal samples collected by the MPD from the patient. Each iteration of the analysis program analyzes a new group of samples and produces either a treat result, indicating that the patient should be treated, or a do not treat result, indicating that the patient should not be treated. Each processor counts the number of treat results and do not treat results it has reached. In the ANALYZE STATE 231, 233, when the treat result count of both of the processors 104, 105 reaches a charge threshold, which is preferably equal to one, these advance the treatment subsystem to CHARGING STATE 232, triggering the charging circuit 107 to begin accumulating a charge in the treatment subsystem.

The charging of the treatment subsystem 108 by the charging circuit 107 is preferably also protected by a processor-redundant system. The operator is preferably able to use treatment voltage controls, such as an "increase voltage" button (not shown), and a "decrease voltage" button (not shown) to control the voltage to which the treatment subsystem 106 is charged. When the operator uses the treatment voltage controls to select a voltage to which the treatment subsystem 106 should be charged, the selected voltage is communicated to the main processor 104. The main processor 104 stores the selected voltage and transmits a message to the auxiliary processor 105 that indicates the selected voltage and instructs the auxiliary processor 105 to set the treatment voltage to match the selected voltage. The auxiliary processor 105 returns a message to the main processor 104 containing the selected voltage so that the main processor 104 may check that the auxiliary processor 105 received it correctly. The auxiliary processor 105 also sends an indication of the selected voltage to a D/A converter 1.03, which converts the digital indication of the selected voltage to an analog indication of the selected voltage. This analog indication of the selected voltage is the input to one side of a charging comparator (not shown in FIG. 1) in the charging circuit 107 that regulates the accumulation of charge in the treatment subsystem 106. The input for the other side of the charging comparator is the voltage across a capacitor (not shown in FIG. 1) in the treatment subsystem 106 in which charge is accumulated. When the signals from both processors 104, 105 to begin charging are received to advance the treatment subsystem 106 to the charging state, the capacitor begins to accumulate charge and the voltage across it increases. When the voltage across the comparator has increased to match the analog indication of the selected voltage, the output of the comparator changes, the charging is halted, and a charging complete signal is sent to both processors 104, 105. The voltage across the capacitor is convened to digital form by another D/A converter and is read by both processors 104, 105 in distal form to determine whether the actual capacitor voltage matches, within tolerance, the selected voltage. If not, each processor enters the DISABLED STATE, preventing the MPD from proceeding to treat the patient. Also, during charging, both processors 104, 105 preferably to check to see whether charging is taking longer than a maximum charging time. If so, the processors enter the DISABLED STATE.

In the ANALYZE STATE 23 1 (FIG. 2), when the main processor's treat result count reaches a treat threshold, which is preferably equal to two, it proceeds to TREAT STATE 241. Similarly, in the ANALYZE STATE 233, the auxiliary, processor 105 also proceeds to TREAT STATE 243 when its treat result count reaches the treat threshold. On the other hand, if, in the ANALYZE STATE 231, the main processors DO NOT TREAT result count reaches a DO NOT TREAT threshold, preferably equal to two, the main processor 104 proceeds to DO NOT TREAT STATE 261. The DO NOT TREAT STATE 261 is designed to prevent the treatment of the patient and dissipate any charge accumulated in the treatment subsystem 106 by discharging it internally. Similarly, if, in the ANALYZE STATE 231, the auxiliary processor's DO NOT TREAT result count reaches the DO NOT TREAT threshold, the auxiliary processor proceeds to DO NOT TREAT STATE 263.

The TREAT STATE 241 is designed to treat the patient by delivering the charge accumulated in the treatment subsystem 106 if a deliver button is pressed by the operator in a semiautomatic system. In the TREAT STATE 241, if the deliver button is pressed, the main processor 104 sends a message to the auxiliary, processor 105 that the deliver button has been pressed and signals the delivery, circuit 108 to deliver the charge accumulated in the treatment subsystem 106 to the patient. In the TREAT STATE 243, if the deliver button is pressed and the auxiliary processor 105 receives a message from the main processor 104 that the deliver button has been pressed, the auxiliary processor 105 signals the delivery circuit 108 to deliver the charge accumulated in the treatment subsystem to the patient. In the CHARGING STATE 232, if charging is complete and both processors 104, 105 signal the treatment subsystem 106 to deliver the charge accumulated in the treatment subsystem 106 to the patient, then the treatment subsystem 106 proceeds to PATIENT DELIVERY STATE 252 and delivers the charge accumulated in the treatment subsystem to the patient. If the deliver button is not depressed within a predetermined period of time, each processor 104, 106 proceeds to the DO NOT TREAT STATE 261, 263 followed by the IDLE STATE 211, 213. When either processor 104, 105 enters the DO NOT TREAT STATE 261, 263, it advances the treatment subsystem to CHARGE DISSIPATE STATE 262. In the charge DISSIPATE STATE 262, the treatment subsystem internally discharges any charge accumulated in the CHARGING STATE 232. In an alternate embodiment, the treatment subsystem delivers any charge accumulated in the CHARGING STATE to ground.

An Analyze program is executed by both processors 104, 105 in the ANALYZE STATE 231, 233 to analyze EGG samples (samples). The Analyze program analyzes samples in groups, reaching either a TREAT result or a DO NOT TREAT result for each group. The program keeps track of the number of TREAT results and DO NOT TREAT results, and continues to analyze further groups of samples until either the number of TREAT results or the number of DO NOT TREAT results reach a predetermined threshold. At this point, the program has reached a final result, analysis is complete, mad the program causes the processor to proceed to either the TREAT STATE 241, 243 or the DO NOT TREAT STATE 261, 263.

Figure 3:
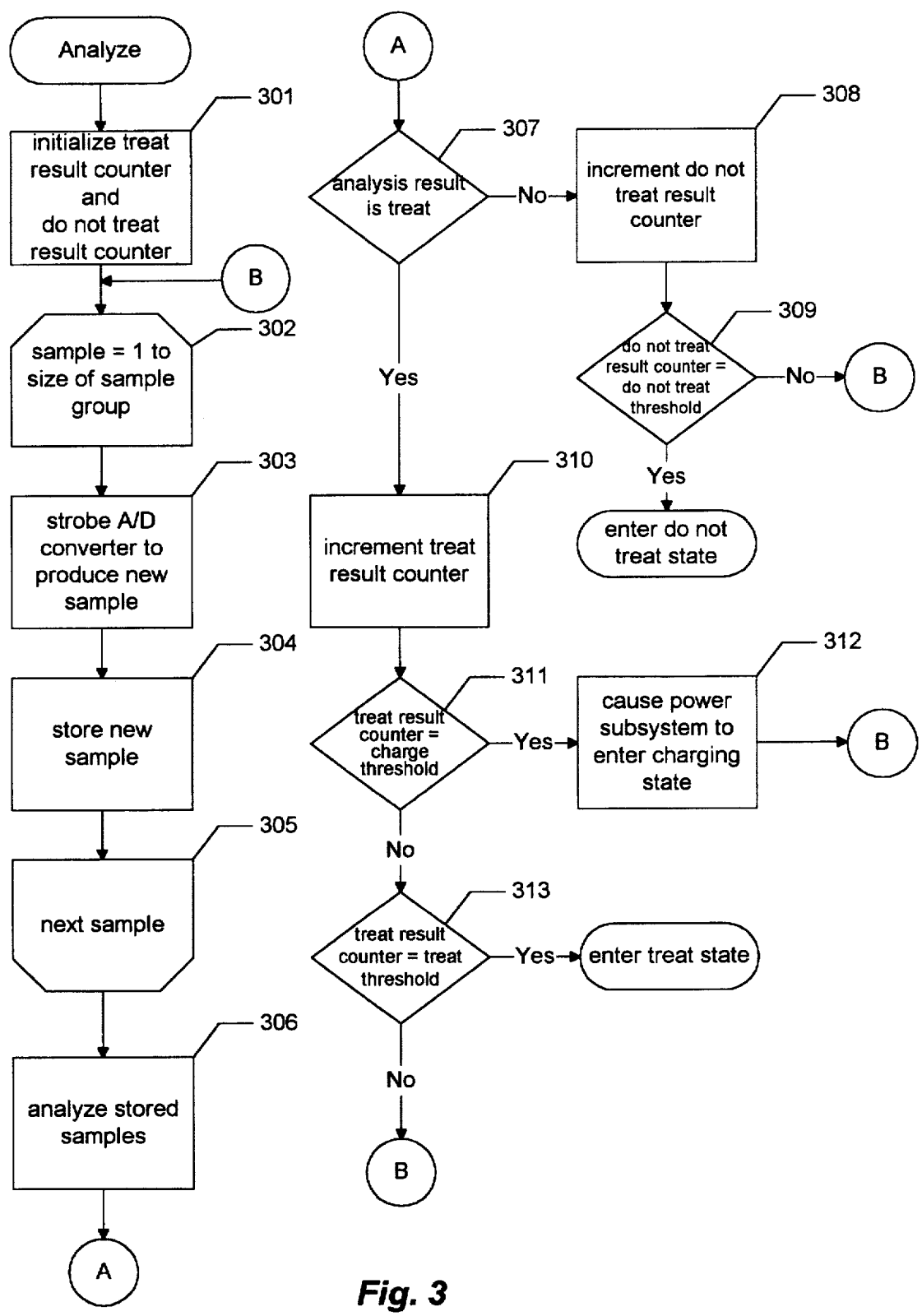
FIG. 3 is a flow diagram of the Analyze program.

FIG. 3 is a flow diagram of the Analyze program. In step 301, the program initializes a TREAT result counter and a DO NOT TREAT result counter by setting each equal to zero. The TREAT result counter is a variable that contains the number of treat results reached by the program, and the DO NOT TREAT result counter contains the number of DO NOT TREAT results reached by the program. In steps 302–306, the program collects and analyzes a group of samples. Step 302 marks the beginning of a loop for collecting each sample of the group, and contains the loop boundaries. The loop is repeated for each value of sample between 1 and the size of a sample group, which is preferably equal to 300. In step 303, the program strobes the A/D converter 103 to produce a new sample. Step 303 is preferably only executed by the main processor 104, as it alone is responsible for strobing the A/D converter 103. In step 304, the program stores the new sample for later analysis. Step 305 marks the end of the loop. In step 306, the program analyzes the group of samples collected and stored in steps 302–305. After analyzing the loop, the program continues through connector A to step 307.

In step 307, if the result of the analysis is the TEAT result, then the program continues at step 310, else the program continues at step 308. In step 308, the program increments the DO NOT TREAT result counter to reflect the DO NOT TREAT result reached in analyzing the group of samples. In step 309, if the DO NOT TREAT result counter equals the DO NOT TREAT threshold, preferably equal to two, then the program concludes and the processor 104, 105 enters the DO NOT TREAT STATE 261, 263, else the program continues through connector B at step 302 to analyze another group of samples.

If the program determined at step 307 that treatment is indicated, it increments the TREAT result counter at step 310 to reflect the treat result reached in analyzing the group of samples. In step 311, if the TREAT result counter is equal to the charge threshold, preferably equal to one, then the program continues at step 312, else the program continues at step 313. In step 312, the program causes the treatment subsystem 108 to enter the CHARGING STATE 232 by triggering the charging circuit. In the auxiliary processor, step 312 involves sending an enable signal to the charging circuit, allowing it to be triggered by the main processor. In the main processor 104, step 312 involves triggering the charging circuit once it has been enabled by the auxiliary processor 105. The program then continues through connector B at step 302 to analyze another group of samples. In step 313, if the treat result counter equals the treat threshold, then the program concludes and the processor 104, 105 enters the TREAT STATE 241, 243, else the program continues through connector B at step 302 to analyze another group of samples.

While this invention has been shown and described with reference to preferred embodiments, it will be understood by those skilled in the art that various changes or modifications in form and detail may be made without departing from the scope of the invention. For example, the MPD could contain three or more processors for redundantly analyzing ECG signals and controlling defibrillation. Also, to further automate the operation of the MPD, the analyze button pressed condition for proceeding to the ANALYZE STATE may be omitted, as may the deliver button pressed condition for proceeding to the PATENT DELIVERY STATE.

We claim:

1. A method for using redundant processing to perform automatic or semi-automatic defibrillation by determining whether a defibrillation shock should be delivered to a patient, the method comprising the steps of:

analyzing electrocardiogram signals from the patient under the control of a first processor in order to determine whether the patient should be treated;

analyzing electrocardiogram signals from the patient under the control of a second processor in order to determine whether the patient should be treated; and if the analysis under the control of the second processor determines that the patient should be treated and the analysis under the control of the first processor determines that the patient should be treated, determining that a defibrillation charge should be delivered to the patient.

2. The method of claim 1, further including the step of, if the determining step determined that a defibrillation charge should be delivered to the patient, delivering a defibrillation charge to the patient.

3. The method of claim 2, further including the steps of, if the determining step determined that a defibrillation charge should be delivered to the patient:

displaying a visual indication that a defibrillation charge should be delivered to the patient; and receiving a delivery instruction from an operator before performing the step of delivering a defibrillation charge to the patient.

4. The method of claim 3 wherein the step of receiving a delivery instruction from an operator includes the steps of:

receiving the delivery instruction in the first processor; and receiving the delivery instruction in the second processor.

5. The method of claim 4, further including the steps of:

after receiving the delivery instruction in the first processor, generating a first delivery signal;

after the delivery instruction is received in the second processor, generating a second delivery signal, and performing the step of delivering a defibrillation charge to the patient, only if both a first delivery signal and a second delivery signal have been generated.

6. The method of claim 3, further including the step of receiving an analyze instruction before performing either of the analyzing steps.

7. The method of claim 1, further including the steps of:

performing a diagnostic test on the first processor to determine whether the first processor is functioning properly;

communicating a result of the diagnostic test to the second processor, wherein the result is positive if the first processor is functioning properly and wherein the result is negative if the first processor is not functioning properly;

if the result of the diagnostic test is positive, performing the step of analyzing electrocardiogram signals from the patient under the control of the first processor; and if the result of the diagnostic test is negative, disabling the step of analyzing electrocardiogram signals from the patient under the control of the first processor.

8. The method of claim 1 wherein the electrocardiogram signals are received from the patient via dual-purpose electrodes capable of both conveying electrocardiogram signals and delivering defibrillation charges which are connected to electrode connections, further including the steps of:

determining whether an impedance across the electrode connections is within an acceptable range for a combined impedance of typical dual-purpose electrodes and a typical patient;

if it is determined that the impedance across the electrode connections is within the acceptable range for the combined impedance of typical dual-purpose electrodes and a typical patient, performing the analyzing steps; and if it is determined that the impedance across the electrode connections is not within the acceptable range for the combined impedance of typical dual-purpose electrodes, inhibiting the analyzing steps.

9. The method of claim 1, further including the step of disabling the analyzing steps if the analysis under the control of only one of the first processor and the second processor determines that the patient should be treated.

10. The method of claim 1 wherein the method is performed in an electronic device capable of accumulating an electrical charge, and wherein the analyzing steps produce a preliminary determination of whether the patient should be treated, further including the step of:

if the preliminary determination produced by the analysis under control of both processors is that the patient should be treated, accumulating an electrical charge in the electronic device.

11. The method of claim 10 wherein the step of accumulating an electrical charge in the electronic device includes the steps of:

sending an indication of a selected charge magnitude from the first processor to the second processor; and accumulating the selected magnitude of charge in the electronic device under the control of the second processor.

12. The method of claim 10, further including the steps of:

receiving from an operator an indication of the selected magnitude of charge in the first processor; and displaying to the operator the selected magnitude of charge received in the second processor.

13. The method of claim 10, further including the step of, if the charging step is not completed within an interval of preselected length, disabling the analyzing steps.

14. The method of claim 1 wherein the method is performed in an electronic device capable of accumulating an electrical charge, further including the step of, if the analysis under the control of the first processor determines that the patient should be not be treated or the analysis under the control of the second processor determines that the patient should not be treated, and if an electrical charge has been accumulated in the electronic device, dissipating the accumulated electrical charge.

15. The method of claim 1, farther including the steps of:

in each processor, periodically transmitting an indication that the analyzing step is proceeding normally to the other processor; and in each processor, if no indication that the analysis of the other processor is proceeding normally is received during a period of predetermined length, terminating the analyzing steps.

16. In a computer system having at least two microprocessors, a method for analyzing electrocardiogram samples from a patient to determine whether the patient should be defibrillated, the method comprising the steps of:

in each microprocessor, successively analyzing each of a plurality of groups of electrocardiogram samples to produce a result for each group for each microprocessor, the result being either a treat result if the analysis shows that the patient should be defibrillated or a do not treat result if the analysis shows that the patient should not be defibrillated;

for each microprocessor, maintaining a count of the number of treat results produced by the microprocessor and a count of the number of do not treat results produced by the microprocessor;

if the counts of the number of treat results produced by both microprocessors exceeds a treatment threshold, determining that the patient should be defibrillated; and if the count of the number of do not treat results produced by either microprocessor exceeds a non-treatment threshold, determining that the patient should not be defibrillated.

17. The method of claim 16, further including the step of, if the counts of the number of treat results produced by the microprocessors are unequal, disabling the computer system.

18. The method of claim 16 wherein the electrocardiogram samples are received from the patient via dual-purpose electrodes capable of both conveying electrocardiogram signals and delivering defibrillation charges, the dual-purpose electrodes being connected to electrode connections, further including the step of, before performing the analyzing step, determining that the impedance across the electrode connections is within an acceptable range for the combined impedance of typical dual-purpose electrodes and a typical patient.

19. The method of claim 16, further including the steps of:

in each microprocessor, during a predetermined interval, determining whether the processor is operating correctly;

in each processor, if it is determined that the processor is operating correctly, sending a signal indicating that the processor is working correctly to the other processor; and in each processor, if the predetermined interval expires before a signal indicating that the other processor is operating correctly is received, disabling the computer system.

20. A dual processor semi-automatic defibrillator, comprising:

a first processor for analyzing electrocardiogram signals from a patient and producing either a treat result if the analysis shows that the patient should be treated or a do not treat result if the analysis shows that the patient should not be treated;

a second processor for analyzing the same electrocardiogram signals analyzed by the first processor and producing either a treat result if the analysis shows that the patient should be treated or a do not treat result if the analysis shows that the patient should not be treated; and a treatment subsystem coupled to receive either a treat result or a do not treat result from each of the processors, the treatment subsystem for defibrillating the patient if and only if both the first processor and the second processor produce a treat result.

21. The defibrillator of claim 20, further comprising:

a communications link connecting the first processor and the second processor;

in the first processor, an operations monitor for periodically determining whether the first processor is operating correctly, and, if so, transmitting a signal to the second processor via the communications link indicating that the first processor is operating correctly; and in the second processor, a signaling monitor for receiving from the first processor via the communications link signals indicating that the first processor is operating correctly, comprising:

a signal reception timer for producing a termination signal an interval greater than a predetermined signaling interval has elapsed since the last signal indicating that the first processor is operating correctly was received from the first processor via the communications link, and a defibrillation terminator coupled to receive the termination signal from the signal reception timer and coupled to terminate the defibrillation activities of the defibrillator upon receipt of the termination signal.

22. The defibrillator of claim 21, further comprising:

a capacitor from which a defibrillation charge is delivered to the patient by the treatment subsystem; and a charging actuator connected to the capacitor and both microprocessors which charges the capacitor to the desired energy level if and only if charging actuation signals are received from each processor.

23. The defibrillator of claim 22, further comprising a charging energy control system, comprising:

a desired energy indication generator for generating an indication of the desired energy to which the capacitor should be charged when charging is actuated by the charging actuator;

a charging complete indication transmitter coupled to transmit an indication to at least one of the processors that the capacitor has been completely charged to the desired energy; and an actual charged energy indication transmitter coupled to transmit to at least one of the microprocessors an indication of the actual energy accumulated in the capacitor.

24. The defibrillator of claim 20, wherein the treatment subsystem comprises:

a charging circuit for accumulating a defibrillation charge;

a patient delivery circuit coupled to deliver the defibrillation charge from the capacitor to the patient if and only if both the first processor and the second processor produce a treat result; and an internal discharge circuit coupled to dissipate the defibrillation charge from the capacitor if either the first processor or the second processor produce a do not treat result.

25. The defibrillator of claim 24, further comprising:

dual-purpose electrodes connected to the first processor, the second processor, and the patient delivery circuit at a first end and adapted to be connected to the patient at a second end for both conveying electrocardiogram signals from the patient to the first processor and the second processor and delivering the defibrillation charge from the patient delivery circuit to the patient: and an impedance fail-safe subsystem for determining whether the impedance across the dual-purpose electrodes is within an acceptable range for the combined impedance of typical dual-purpose electrodes and a typical patient and, if not, preventing the delivery of the defibrillation charge to the patient.

26. The defibrillator of claim 24, further comprising:

in the first processor, a first charging initiator for initiating the accumulation of charge in the charging circuit;

in the second processor, a second charging initiator for initiating the accumulation of charge in the charging circuit: and a charging controller for causing the charging circuit to begin accumulating a defibrillation charge if and only if both the first charging initiator and the second charging initiator initiate the accumulation of charge in the charging circuit.

27. The defibrillator of claim 20, further comprising a treatment actuator for use by an operator to actuate defibrillation by the treatment subsystem, and wherein the treatment subsystem defibrillates the patient if and only if the operator actuates the treatment actuator.

28. The defibrillator of claim 20, further including signal processor for processing the electrocardiogram signals into a form in which the first processor and the second processor may analyze them.

29. A redundant electrocardiogram analysis system for an automatic or semi-automatic defibrillator, comprising:

an analog-to-digital converter for receiving and converting to digital form electrocardiogram signals from a patient;

a main processor for analyzing the electrocardiogram signals converted to digital form by the analog-to-digital converter;

an auxiliary processor for analyzing the electrocardiogram signals converted to digital form by the analog-to-digital converter;

a treatment subsystem for determining that a charge should be delivered to the patient when both the main processor and the auxiliary processor determine that the patient should be treated.

30. The defibrillator of claim 29, further including a clock for strobing the analog-to-distal converter to convert to digital form the ECG signal presently being received from the patient.

31. The defibrillator of claim 29, wherein the treatment subsystem comprises:

a charging circuit for accumulating a defibrillation charge;

a patient delivery circuit for delivering the defibrillation charge to the patient if and only if both the first processor and the second processor produce a treat result; and an internal discharge circuit for dissipating the defibrillation charge if either the first processor or the second processor produce a do not treat result.

32. The defibrillator of claim 31 wherein the main processor contains a charging initiator for causing the charging circuit to begin accumulating a defibrillation charge.

33. The defibrillator of claim 29, further including:

a communications link between the main processor and the auxiliary processor for transmitting status information between the main processor and the auxiliary processor to determine if the analysis of the main processor and the analysis of the auxiliary processor are proceeding properly; and a defibrillator disabler for disabling the defibrillator if it is determined that the analysis of the main processor or the analysis of the auxiliary processor is not proceeding properly.

34. A method for using redundant processing to perform automatic or semi-automatic defibrillation by determining whether a defibrillation shock should be delivered to a patient, the method comprising the steps of:

analyzing electrical signals from the patient under the control of a first processor in order to determine whether the patient should be treated;

analyzing electrical signals from the patient under the control of a second processor in order to determine whether the patient should be treated; and if the analysis under the control of the second processor determines that the patient should be treated and the analysis under the control of the first processor determines that the patient should be treated, determining that a defibrillation charge should be delivered to the patient.

35. The method of claim 34 wherein the analyzing steps each analyze electrocardiogram signals from the patient.

36. A dual processor semi-automatic defibrillator, comprising:

a first processor for analyzing electrical signals from a patient and producing either a treat result if the analysis shows that the patient should be treated or a do not treat result if the analysis shows that the patient should not be treated;

a second processor for analyzing the same electrical signals analyzed by the first processor and producing either a treat result if the analysis shows that the patient should be treated or a do not treat result if the analysis shows that the patient should not be treated; and a treatment subsystem coupled to receive either a treat result or a do not treat result from each of the processors, the treatment subsystem for defibrillating the patient if and only if both the first processor and the second processor produce a treat result.

37. The defibrillator of claim 36 wherein each processor contains an electrocardiogram signal analyzer for analyzing electrocardiogram signals from the patient, and wherein each processor produces either a treat result or a do not treat result based upon the electrocardiogram signal analysis of its electrocardiogram signal analyzer.

* * * * *

UNITED STATES PATENT AND TRADEMARK OFFICE
CERTIFICATE OF CORRECTION

PATENT NO. : 5,496,349
DATED : March 5, 1996
INVENTOR(S) : D.D. Campbell et al.

It is certified that error appears in the above-indentified patent and that said Letters Patent is hereby corrected as shown below:

| COLUMN | LINE | |
|---|---|---|
| [54] | Title | "DEFILBRILLATION" should read --DEFIBRILLATION-- |
| 1 | 2 | "DEFILBRILLATION" should read --DEFIBRILLATION-- |
| 2 | 42 | "Became" should read --Because-- |
| 5 | 34 | "convened" should read --converted-- |
| 5 | 35 | "distal" should read --digital-- |
| 6 | 24 | "EGG" should read --ECG-- |
| 6 | 33 | "mad" should read --and-- |
| 6 | 57 | "TEAT" should read --TREAT-- |
| 7 | 31 | "PATENT" should read --PATIENT-- |

UNITED STATES PATENT AND TRADEMARK OFFICE
CERTIFICATE OF CORRECTION

PATENT NO. : 5,496,349
DATED : March 5, 1996
INVENTOR(S) : D.D. Campbell et al.

It is certified that error appears in the above-indentified patent and that said Letters Patent is hereby corrected as shown below:

| COLUMN | LINE | |
|---|---|---|
| 9 (Claim 15, | 17 line 1) | "farther" should read --further-- |
| 11 (Claim 30, | 65 line 2) | "analog-to-distal" should read --analog-to-digital-- |

Signed and Sealed this

Tenth Day of December, 1996

Attest:

BRUCE LEHMAN

*Attesting Officer*     *Commissioner of Patents and Trademarks*